US006546927B2

(12) United States Patent
Litherland et al.

(10) Patent No.: US 6,546,927 B2
(45) Date of Patent: Apr. 15, 2003

(54) METHODS AND APPARATUS FOR CONTROLLING PIEZOELECTRIC VIBRATION

(75) Inventors: Craig Litherland, Cupertino, CA (US); Rob Burnside, Mountain View, CA (US); Kamran Behzadian, Sunnyvale, CA (US); Michael Klimowicz, Los Altos, CA (US)

(73) Assignee: Aerogen, Inc., Sunnyvale, CA (US)

( * ) Notice: Subject to any disclaimer, the term of this patent is extended or adjusted under 35 U.S.C. 154(b) by 0 days.

(21) Appl. No.: 09/805,498

(22) Filed: Mar. 13, 2001

(65) Prior Publication Data

US 2002/0129813 A1 Sep. 19, 2002

(51) Int. Cl.$^7$ ............................................. A61M 11/00
(52) U.S. Cl. ............................. 128/200.16; 128/200.14
(58) Field of Search ................. 128/200.14, 200.16, 128/200.18, 200.23, 202.25, 203.12, 203.15, 203.27; 239/3, 690, 706

(56) References Cited

U.S. PATENT DOCUMENTS

| 2,101,304 A | 12/1937 | Wright | 120/50 |
| 2,158,615 A | 5/1939 | Wright | 120/50 |

(List continued on next page.)

FOREIGN PATENT DOCUMENTS

| CH | 477 885 | 10/1969 |
| CH | 555 681 | 9/1974 |
| EP | 0 049 636 A2 | 4/1982 |
| EP | 0 134 847 A1 | 3/1985 |
| EP | 0 178 925 | 4/1986 |
| EP | 0 387 222 A1 | 3/1990 |
| EP | 0 516 565 A1 | 5/1992 |
| EP | 0 542 723 A2 | 5/1993 |
| EP | 0 476 991 B1 | 3/1995 |
| FR | 2 692 569 A1 | 6/1992 |
| GB | 973458 | 10/1964 |
| GB | 1454597 | 11/1976 |
| GB | 2 073 616 A | 10/1981 |
| GB | 2 101 500 | 1/1983 |
| GB | 2 177 623 A | 1/1987 |
| GB | 2 240 494 A | 8/1991 |
| GB | 2 272 389 A | 5/1994 |
| GB | 2 279 571 A | 1/1995 |
| JP | 57-23852 | 2/1982 |
| JP | 57-105608 | 7/1982 |
| JP | 58-61857 | 4/1983 |
| JP | 58-139757 | 8/1983 |
| JP | 60-4714 A | 1/1985 |
| JP | 61-8357 A | 1/1986 |
| JP | 61-215059 A | 9/1986 |
| JP | 2-135169 | 5/1990 |
| JP | 2-189161 | 7/1990 |
| WO | WO 92/07600 | 5/1992 |
| WO | WO 92/11050 | 7/1992 |
| WO | WO 93/01404 | 1/1993 |
| WO | WO 96/09229 | 3/1996 |
| WO | WO 99/63946 | 12/1999 |

OTHER PUBLICATIONS

Berglund, R.N., et al. Generation of Monodisperse Aerosol Standards. Environ. Sci. Technology 7:2:147 (1973).

(List continued on next page.)

*Primary Examiner*—Aaron J. Lewis
*Assistant Examiner*—Teena Mitchell
(74) *Attorney, Agent, or Firm*—Townsend and Townsend and Crew LLP

(57) ABSTRACT

A method for aerosolizing a liquid comprises providing an aerosol generator having a plate with a plurality of apertures and a piezoelectric element to vibrate the plate. Liquid is supplied to the plate, and the piezoelectric element is energized to vibrate the plate at an initial frequency. The energy level is adjusted to vibrate the plate at its instantaneous resonant frequency during aerosolization of the liquid.

41 Claims, 4 Drawing Sheets

U.S. PATENT DOCUMENTS

| | | | | |
|---|---|---|---|---|
| 2,187,528 A | 1/1940 | Wing | | 120/50 |
| 2,223,541 A | 12/1940 | Baker | | 120/50 |
| 2,266,706 A | 12/1941 | Fox et al. | | 128/173 |
| 2,283,333 A | 5/1942 | Martin | | 120/50 |
| 2,292,381 A | 8/1942 | Klagges | | 120/50 |
| 2,360,297 A | 10/1944 | Wing | | 120/52 |
| 2,375,770 A | 5/1945 | Dahlberg | | 120/52 |
| 2,404,063 A | 7/1946 | Healy | | 120/51 |
| 2,430,023 A | 11/1947 | Longsmaid | | 120/52 |
| 2,474,996 A | 7/1949 | Wallis | | 120/52 |
| 2,512,004 A | 6/1950 | Wing | | 120/52 |
| 2,521,657 A | 9/1950 | Severy | | 120/50 |
| 2,681,041 A | 6/1954 | Zodtner et al. | | 120/50 |
| 2,779,623 A | 1/1957 | Eisenkraft | | 299/1 |
| 2,935,970 A | 5/1960 | Morse et al. | | 120/52 |
| 3,411,854 A | 11/1968 | Rosler et al. | | 401/227 |
| 3,558,052 A | 1/1971 | Dunn | | 293/3 |
| 3,738,574 A | 6/1973 | Gunterdorfer et al. | | 239/102 |
| 3,790,079 A | 2/1974 | Berglund et al. | | 239/3 |
| 3,804,329 A | 4/1974 | Martner | | 239/4 |
| 3,812,854 A | 5/1974 | Michaels et al. | | 128/194 |
| 3,950,760 A | 4/1976 | Stromberger et al. | | 346/140 |
| 3,958,249 A | 5/1976 | DeMaine et al. | | 346/1 |
| 3,983,740 A | 10/1976 | Danel | | 73/12 |
| 4,005,435 A | 1/1977 | Lundquist et al. | | 346/1 |
| 4,109,174 A | 8/1978 | Hodgson | | |
| 4,119,096 A | 10/1978 | Drews | | 128/194 |
| 4,159,803 A | 7/1979 | Cameto et al. | | 239/102 |
| 4,226,236 A | 10/1980 | Genese | | 604/89 |
| 4,240,081 A | 12/1980 | Devitt | | 346/75 |
| 4,261,512 A | 4/1981 | Zierenberg | | 239/102 |
| 4,268,460 A | 5/1981 | Boiarski et al. | | 261/1 |
| 4,294,407 A | 10/1981 | Reichl et al. | | 239/102 |
| 4,300,546 A | 11/1981 | Kruber | | 128/200 |
| 4,301,093 A | 11/1981 | Eck | | 261/1 |
| 4,334,531 A | 6/1982 | Reichl et al. | | 128/200.14 |
| 4,336,544 A | 6/1982 | Donald et al. | | 346/1.1 |
| 4,338,576 A | 7/1982 | Takahashi et al. | | 331/67 |
| 4,368,476 A | 1/1983 | Uehara et al. | | 346/140 R |
| 4,389,071 A | 6/1983 | Johnson, Jr. et al. | | 299/14 |
| 4,408,719 A | 10/1983 | Last | | 239/102 |
| 4,431,136 A | 2/1984 | Janner et al. | | 239/102 |
| 4,454,877 A | 6/1984 | Miller et al. | | 128/200.21 |
| 4,465,234 A | 8/1984 | Maehara et al. | | 239/102 |
| 4,474,251 A | 10/1984 | Johnson, Jr. | | 175/67 |
| 4,474,326 A | 10/1984 | Takahashi | | 239/102 |
| 4,475,113 A | 10/1984 | Lee et al. | | 346/1.1 |
| 4,479,609 A | 10/1984 | Maeda et al. | | 239/102 |
| 4,530,464 A | 7/1985 | Yamamoto et al. | | 239/102 |
| 4,533,082 A | 8/1985 | Maehara et al. | | 239/102 |
| 4,539,575 A | 9/1985 | Nilsson | | 346/140 R |
| 4,544,933 A | 10/1985 | Heinzl | | 346/140 R |
| 4,546,361 A | 10/1985 | Brescia et al. | | 346/140 R |
| 4,550,325 A | 10/1985 | Viola | | 346/140 R |
| 4,591,883 A | 5/1986 | Isayama | | 346/140 R |
| 4,593,291 A | 6/1986 | Howkins | | 346/1.1 |
| 4,605,167 A | 8/1986 | Maehara | | 239/102 |
| 4,620,201 A | 10/1986 | Heinzl et al. | | 346/140 R |
| 4,628,890 A | 12/1986 | Freeman | | 123/593 |
| 4,632,311 A | 12/1986 | Nakane et al. | | 239/101 |
| 4,659,014 A | 4/1987 | Soth et al. | | 239/102.2 |
| 4,681,264 A | 7/1987 | Johnson, Jr. | | 239/589.1 |
| 4,702,418 A | 10/1987 | Carter et al. | | 239/101 |
| 4,722,906 A | 2/1988 | Guire | | 436/501 |
| 4,753,579 A | 6/1988 | Murphy | | 417/322 |
| 4,790,479 A | 12/1988 | Matsumoto et al. | | 239/102.2 |
| 4,793,339 A | 12/1988 | Matsumoto et al. | | 128/200.16 |
| 4,796,807 A | 1/1989 | Bendig et al. | | 239/102.2 |
| 4,799,622 A | 1/1989 | Ishikawa et al. | | 239/102.2 |
| 4,826,759 A | 5/1989 | Guire et al. | | 435/4 |
| 4,828,886 A | 5/1989 | Hieber | | 427/422 |
| 4,850,534 A | 7/1989 | Takahashi et al. | | 239/102.2 |
| 4,865,006 A | 9/1989 | Nogi et al. | | 123/590 |
| 4,877,989 A | 10/1989 | Drews et al. | | 310/323 |
| 4,888,516 A | 12/1989 | Daeges et al. | | 310/323 |
| 4,968,299 A | 11/1990 | Ahlstrand et al. | | 604/90 |
| 4,973,493 A | 11/1990 | Guire | | 427/2 |
| 4,976,259 A | 12/1990 | Higson et al. | | 128/200.18 |
| 4,979,959 A | 12/1990 | Guire | | 623/66 |
| 4,994,043 A | 2/1991 | Ysebaert | | 604/90 |
| 5,002,582 A | 3/1991 | Guire et al. | | 623/66 |
| 5,021,701 A | 6/1991 | Takahashi et al. | | 310/345 |
| 5,063,396 A | 11/1991 | Shiokawa et al. | | 346/140 R |
| 5,063,922 A | 11/1991 | Hakkinen | | 128/200.16 |
| 5,073,484 A | 12/1991 | Swanson et al. | | 435/7.92 |
| 5,076,266 A | 12/1991 | Babaev | | 128/200.16 |
| 5,080,649 A | 1/1992 | Vetter | | 604/191 |
| 5,086,785 A | 2/1992 | Gentile et al. | | 128/782 |
| 5,115,803 A | 5/1992 | Sioutas | | 128/200.23 |
| 5,115,971 A * | 5/1992 | Greenspan et al. | | 239/3 |
| 5,139,016 A | 8/1992 | Waser | | 128/200.16 |
| 5,152,456 A | 10/1992 | Ross et al. | | 239/102.2 |
| 5,157,372 A | 10/1992 | Langford | | 338/211 |
| 5,164,740 A | 11/1992 | Ivri | | 346/1.1 |
| 5,170,782 A | 12/1992 | Kocinski | | 128/200.16 |
| 5,180,482 A | 1/1993 | Abys et al. | | 205/224 |
| 5,186,164 A | 2/1993 | Raghurprasad | | 128/200.14 |
| 5,186,166 A | 2/1993 | Riggs et al. | | 128/203.15 |
| 5,198,157 A | 3/1993 | Bechet | | 264/9 |
| 5,217,492 A | 6/1993 | Guire et al. | | 623/11 |
| 5,258,041 A | 11/1993 | Guire et al. | | 623/66 |
| 5,261,601 A | 11/1993 | Ross et al. | | 239/102.2 |
| 5,263,992 A | 11/1993 | Guire | | 623/66 |
| 5,297,734 A | 3/1994 | Toda | | 239/102.2 |
| 5,299,739 A | 4/1994 | Takahashi et al. | | 239/102.2 |
| 5,309,135 A | 5/1994 | Langford | | 388/211 |
| 5,312,281 A | 5/1994 | Takashashi et al. | | 446/25 |
| 5,320,603 A | 6/1994 | Vetter et al. | | 604/89 |
| 5,347,998 A | 9/1994 | Hodson et al. | | 128/200.23 |
| 5,414,075 A | 5/1995 | Swan et al. | | 568/333 |
| 5,415,161 A | 5/1995 | Ryder | | 128/200.23 |
| 5,431,155 A | 7/1995 | Marelli | | 128/200 |
| 5,435,282 A | 7/1995 | Haber et al. | | 128/200.16 |
| 5,452,711 A | 9/1995 | Gault | | 128/200.14 |
| 5,458,135 A | 10/1995 | Patton et al. | | 128/200.14 |
| 5,477,992 A | 12/1995 | Jinks et al. | | 222/402.2 |
| 5,487,378 A | 1/1996 | Robertson et al. | | 128/200.16 |
| 5,489,266 A | 2/1996 | Grimard | | 604/82 |
| 5,511,726 A * | 4/1996 | Greenspan et al. | | 239/102.2 |
| 5,512,329 A | 4/1996 | Guire | | 427/508 |
| 5,512,474 A | 4/1996 | Clapper et al. | | 435/240.243 |
| 5,515,841 A | 5/1996 | Robertson et al. | | 128/200.16 |
| 5,515,842 A | 5/1996 | Lamseyev et al. | | 128/200.18 |
| 5,518,179 A | 5/1996 | Humberstone et al. | | 239/102.2 |
| 5,529,055 A | 6/1996 | Gueret | | 128/200.16 |
| 5,533,497 A | 7/1996 | Ryder | | 128/200.21 |
| 5,563,056 A | 10/1996 | Swan et al. | | 435/180 |
| 5,579,757 A | 12/1996 | McMahon et al. | | 128/200.21 |
| 5,586,550 A | 12/1996 | Ivri et al. | | 128/200.16 |
| 5,637,460 A | 6/1997 | Swan et al. | | 435/6 |
| 5,654,007 A | 8/1997 | Johnson et al. | | 424/489 |
| 5,654,162 A | 8/1997 | Guire et al. | | 435/7.92 |
| 5,654,460 A | 8/1997 | Rong | | 556/472 |
| 5,665,068 A | 9/1997 | Takamura | | 604/191 |
| 5,692,644 A | 12/1997 | Gueyet | | 222/80 |
| 5,707,818 A | 1/1998 | Chudzik et al. | | 435/7.93 |
| 5,714,360 A | 2/1998 | Swan et al. | | 435/174 |
| 5,714,551 A | 2/1998 | Bezwada et al. | | 525/411 |
| 5,718,222 A | 2/1998 | Lloyd et al. | | 128/200.14 |
| 5,744,515 A | 4/1998 | Clapper | | 523/113 |
| 5,758,637 A | 6/1998 | Ivri et al. | | 128/200.16 |

| | | | | |
|---|---|---|---|---|
| 5,788,819 A | * | 8/1998 | Onishi et al. | 205/155 |
| 5,893,515 A | | 4/1999 | Hahn et al. | 239/7 |
| 5,910,698 A | | 6/1999 | Yagi | 310/316 |
| 5,915,377 A | * | 6/1999 | Coffee | 128/200.14 |
| 5,938,117 A | | 8/1999 | Ivri | 239/4 |
| 5,960,792 A | * | 10/1999 | Lloyd et al. | 128/200.14 |
| 6,012,450 A | | 1/2000 | Rubsamen | 128/200.14 |
| 6,014,970 A | | 1/2000 | Ivri et al. | 128/200.16 |
| 6,062,212 A | | 2/2000 | Davison et al. | 128/200.16 |
| 6,032,665 A | * | 3/2000 | Psaros | 128/203.12 |
| 6,060,128 A | * | 5/2000 | Kim et al. | 427/421 |
| 6,085,740 A | | 6/2000 | Ivri et al. | 128/200.23 |
| 6,105,877 A | * | 8/2000 | Coffee | 128/204.21 |
| 6,142,146 A | * | 11/2000 | Abrams et al. | 128/203.15 |
| 6,152,130 A | * | 11/2000 | Abrams et al. | 128/203.12 |
| 6,196,218 B1 | * | 3/2001 | Voges | 128/200.14 |
| 6,196,219 B1 | * | 3/2001 | Hess et al. | 128/200.14 |
| 6,205,999 B1 | | 3/2001 | Ivri et al. | 128/200.22 |
| 6,235,177 B1 | | 5/2001 | Borland et al. | 205/67 |
| 6,318,640 B1 | * | 11/2001 | Coffee | 128/204.21 |
| 6,328,033 B1 | * | 12/2001 | Avrahami | 128/200.25 |

OTHER PUBLICATIONS

Allen, T. Particle Size Measurement. Chapman and Hall pp. 167–169 (1981).

Ueha, S., et al. Mechanism of Ultrasonic Atomization Using a Multi–Pinhole Plate. J. Acoust. Soc. Jpn. (E) 6,1:21 (1985).

Maehara, N., et al. Influence of the Vibrating System of a Multipinhole–plate Ultrasoic Nebulizer on Its Performance. Review of Scientific Instruments, 57 (11), Nov. 1986, pp. 2870–2876.

Maehara, N., et al. Optimum Design Procedure for Multi–Pinhole–plate Ultrasonic Atomizer. Japanese Journal of Applied Physics, 26:215 (1987).

Ashgriz, N., et al. Development of a Controlled Spray Generator. Rev. Sci. Instrum. 58(7):1291 (1987).

Hikayama, H., et al. Ultrasonic Atomizer with Pump Function. Tech. Rpt. IEICE Japan US88–74:25 (1988).

J. Acousticl Soc. Japan 44:2:116 (1988).

J. Acoustical Soc. Japan 44:6:425 (1988).

Siemens AG, 1989, "Ink–Jet Printing: The Present State Of The Art," by Wolfgang R. Wehl.

TSI Incorporated product catalog. Vibrating Orifice Aerosol Generator (1989).

Gaiser Tool Company catalog, pp. 26, 29–30 (19_).

Nogi, T., et al. Mixture Formation of Fuel Injection System in Gasoline Engine. Nippon Kikai Gakkai Zenkoku Taikai koenkai Koen Ronbunshu 69:660 (1991).

D.C. Cipolla et al., "Assessment of Aerosol Delivery systems for Recomvinant Human Deoxyribonuclease," *S.T.P. Pharma Sciences* 4 (1) 50–62, 1994.

D.C. Cipolla et al., "Characterization of Aerosols of Human Recombinant Deoxyribonuclease I (rhDNase) Generated by Jet Nebulizers," *Pharmaceutical Research* II (4) 491–498, 1994.

I. Gonda, "Therapeutic Aerosols," *Pharmaceutics, The Sci. of Dosage Form Design*, M.E. Aulton, 341–358, 1988.

Anthony J. Hickey, "Pharmaceutical Inhalation Aerosol Technology," *Drugs And The Pharmaceutical Sciences*, (54) 172–173.

J.A. Abys et al., "Annealing Behavior of Palladium–Nickel All Electrodeposits," pp. 1–7.

"Palla Tech Pd an Pd Alloy Processes—Procedure for the Analysis of Additive IVS in Palla Tech Plating Solutions by HPLC," *Technical Bulletin*, Electroplating Chemicals & Services, 029–A, Lucent Technologies, pp. 1–5, 1996.

* cited by examiner

METHODS AND APPARATUS FOR CONTROLLING PIEZOELECTRIC VIBRATION

BACKGROUND OF THE INVENTION

The present invention relates to methods and apparatus for controlling piezoelectric vibration, and in particular for controlling piezoelectric vibration of aerosolizing devices, including, but not limited to, those that are configured to atomize liquid medicaments to be inhaled.

A wide variety of procedures have been proposed to deliver a drug to a patient. Of particular interest to the present invention are drug delivery procedures where the drug is a liquid and is dispensed in the form of fine liquid droplets for inhalation by a patient. A variety of devices have been proposed for forming the dispersion, including air jet nebulizers, ultrasonic nebulizers and metered dose inhalers (MDIs). Air jet nebulizers usually utilize a high-pressure air compressor and a baffle system that separates the small particles from the spray. Ultrasonic nebulizers generate ultrasonic waves with an oscillating piezoelectric crystal to produce liquid droplets. Examples of two such ultrasonic nebulizers are described in U.S. Pat. Nos. 5,261,601 and 4,533,082. Typical MDIs usually employ a gas propellant, such as a CFC, which carries the therapeutic substance and is sprayed into the mouth of the patient.

One exemplary atomization apparatus is described in U.S. Pat. No. 5,164,740, the complete disclosure of which is herein incorporated by reference. The atomization apparatus comprises an ultrasonic transducer and an aperture plate attached to the transducer. The aperture plate includes tapered apertures, which are employed to produce small liquid droplets. The transducer vibrates the plate at relatively high frequencies so that when the liquid is placed in contact with the rear surface of the aperture plate and the plate is vibrated, liquid droplets will be ejected through the apertures. The apparatus described in U.S. Pat. No. 5,164,740 has been instrumental in producing small liquid droplets without the need for placing a fluidic chamber in contact with the aperture plate. Thus, small volumes of liquid are delivered to the rear surface of the aperture plate.

Modified atomization apparatus are described in U.S. Pat. Nos. 5,586,550 and 5,758,637, the complete disclosures of which are herein incorporated by reference. The two references describe a liquid droplet generator, which is particularly useful in producing a high flow of droplets in a narrow size distribution. As described in U.S. Pat. No. 5,586,550, the use of a dome shaped aperture plate is advantageous in allowing more of the apertures to eject liquid droplets.

A variety of drive circuits have been proposed for vibrating piezoelectric crystals. For example, U.S. Pat. No. 4,109,174 describes a drive circuit for a piezoelectric crystal stack. The drive circuitry includes an inductor that allows the mechanically resonant structure to be electrically insensitive to a change in operating frequency. Therefore, the drive circuitry gives rise to operation at a mechanically non-resonance frequency (adjustable between 120 and 145 kHz).

U.S. Pat. No. 5,910,698 describes a methodology for driving piezoelectric vibrated mechanical structures by monitoring certain electrical characteristics, namely voltage, current and the phase difference therebetween. The electrical characteristics are measured at a first frequency where there is no significant vibration, and again at a second frequency where there is a significant vibration. The measured electrical characteristic are used to calculate the current component not relating to vibration, and this in turn is used to calculate the current component attributable to vibration. The calculated vibration current component is then adjusted so that the mechanical structure is driven at the most efficient and stable amplitude. The adjustment is achieved by comparing the calculated vibration current component with a present value, and increasing/decreasing the applied voltage when the calculated component is smaller/greater than the present value, respectively.

The present invention is related to the operation of an aerosol generator at the resonant frequency for as much of the aerosolization process as possible. Given that resonance frequency will change when a load, such as a liquid medicament, is placed on the aperture plate, there is a need to identify and change to the instantaneous resonant frequency as quickly as possible. Hence, in one aspect, the present invention is related to methods and apparatus for readily identifying and changing to the instantaneous resonant frequency of an aerosol generator.

SUMMARY OF THE INVENTION

The invention provides exemplary aerosolization devices and methods for aerosolizing liquids. In one aspect, a method is provided for aerosolizing a liquid utilizing an aerosol generator comprising a plate having a plurality of apertures and a piezoelectric element disposed to vibrate the plate. According to the method, a liquid is supplied to the plate, and the piezoelectric element is energized to vibrate the plate at an initial frequency. The amount of energy supplied to the piezoelectric element is then adjusted to vibrate the plate at a desired frequency during aerosolization of the liquid through the apertures. In this way, the liquid may be aerosolized at the highest volumetric aerosolization rate. In some embodiments, the desired frequency is the instantaneous resonant frequency of the plate, while in other embodiments, the desired frequency is an offset from the instantaneous resonant frequency. In some embodiments, the desired frequency is the anti-resonant frequency.

In one aspect, the energy adjusting step comprises detecting a first value of one or more electrical characteristics (e.g., voltage, current or phase difference between voltage and current) of the piezoelectric element at the initial frequency. The piezoelectric element is then energized to vibrate the plate at a second frequency, with the initial and second frequencies differing from each other by a predetermined amount. A second value of one or more electrical characteristics of the piezoelectric element are detected at the second frequency. The first and second values of the electrical characteristics are then compared before energizing the piezoelectric element at a third frequency. The third frequency is selected based on the comparison between the first and second values of the electrical characteristics. Hence, the change in frequency between the second and third frequencies may be different than the frequency change between the first and second frequencies. For example, the frequency change may be substantially equal to the predetermined amount if the first and second values of the electrical characteristic are substantially equal. When such values are substantially equal, the implication is that the resonant frequency is still some way off, and so there is no need to waste time by changing the frequency by anything less than the predetermined amount. Indeed, the predetermined amount could even be increased. However, if the first and second values significantly differ, the frequency change may be less than the predetermined amount, e.g., inversely proportional to the change in the measured characteristics. Such a difference in the first and second values would be indicative of proximity to the resonant frequency, and thus there is a need to change the frequency by a reduced amount in order to allow accurate determination of the instantaneous resonant frequencies.

The change in frequency may differ from the predetermined amount according to a number of algorithms. For example, as just described the change may be inversely proportional to the change in measured characteristics. Alternatively, other algorithms that may be used to find the resonance frequency include step doubling, bisection, first and second derivative tracking, and the like.

In one aspect, the method may further comprise detecting a third value of the electrical characteristic of the piezoelectric element at the third frequency, and comparing the second and third values. The piezoelectric is energized at a fourth frequency, with the third and fourth frequencies differing from each other by an amount dependent upon the comparison between the second and third values of the electrical characteristics. In other words, the procedure is iterative, with each iteration bringing the vibrational frequency closer to the instantaneous resonant frequency. In some embodiments, the iterations continue until the desired frequency is achieved. In other embodiments, a predetermined number of iterations are done.

In one aspect, the method may further comprise comparing the phase difference between voltage and current at each step. If the phase difference flips or reverses, the resonant frequency has been passed. In some embodiments, a phase locked loop circuit is used to control the frequency at which the piezoelectric plate is vibrated. As such, the frequency may be reduced and the process continued. Further, in some cases the impedance may be measured and analyzed to detect sudden changes in impedance. In this way, the end of the aerosolization event may be detected and, for example, may be used to reduce energization of the piezoelectric element.

In another embodiment, the method may further comprise energizing the piezoelectric element to vibrate the plate at or near its resonant frequency while using minimal power such that liquid is not aerosolized. In this way, the plate is maintained at or near a resonant while using minimal power. Power consumption may be increased to cause the liquid to aerosolize, and the frequency at which the plate was resonated under the minimal power situation may be used as the starting point to locate the resonant frequency under the increased power condition.

In yet another aspect, the method may comprise comparing a parameter indicative of instantaneous resonant frequency with a predetermined range of values. If the predetermined range corresponds to the limits of acceptable aerosolization, an indication of gross device failure may be given when the parameter falls outside the predetermined range of values.

In another embodiment, an aerosolizing apparatus is provided that comprises an aerosol generator having a plate with a plurality of apertures and a piezoelectric element disposed to vibrate the plate. A liquid supply is provided to supply liquid to the plate. The apparatus also comprises an energizing unit that is adapted to energize the piezoelectric element to vibrate the plate at an initial frequency and a controller for controlling the energizing unit. The controller is configured to control energization of the piezoelectric element such that the plate vibrates at its instantaneous resonant frequency during aerosolization of supplied liquid through the apertures. In some embodiments, such controllers comprise a phase locked loop circuit, while in other embodiments, operation of such controllers is primarily controlled by software.

In one aspect, the controller may comprise a detector that is configured to detect a first value of an electrical characteristic of the piezoelectric element at the initial frequency, and a second value of the electrical characteristic of the piezoelectric element at a second frequency. A comparator may be used to compare the first and second values of the electrical characteristic, and a selector may be provided to select a third frequency of energization, with the third frequency differing from the second frequency by an amount that is based upon a comparison of the first and second values of the electrical characteristic.

In other embodiments, a piezoelectric vibration control system is provided in an apparatus having a piezoelectric vibrating element and a vibratable structure to which the piezoelectric vibrating element is attached. The system comprises a detector configured to detect values of an electrical characteristic of the piezoelectric vibrating element at first and a second frequency of vibration. A comparator is configured to compare the detected values of the electrical characteristics, and a selector is configured to select a third frequency of vibration, with the second and third frequencies differing by an amount based upon a difference between the first and second frequency and a comparison of the first and second values of the electrical characteristic.

In yet other embodiments, the piezoelectric vibration control system comprises a phase locked loop circuit capable of tracking operation of the piezoelectric vibrating element and providing a frequency signal to drive a piezoelectric plate.

DESCRIPTION OF THE SPECIFIC EMBODIMENTS

Figure 1:
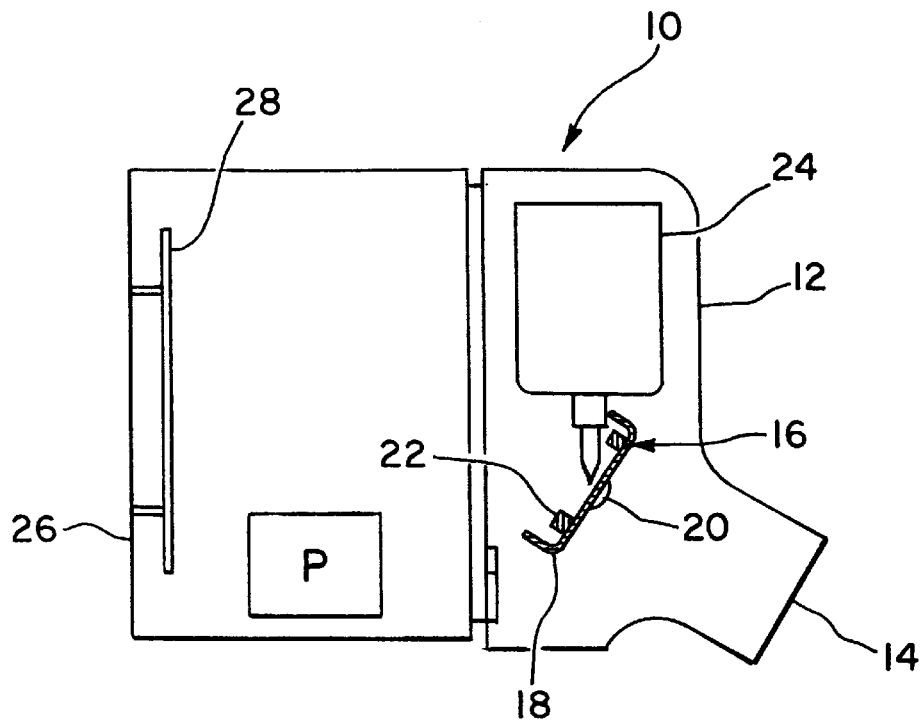
FIG. 1 is a cross-sectional schematic diagram of an aerosolization device according to the invention.

The invention provides exemplary aerosolization devices and methods for aerosolizing liquid supplied to an aerosol generator. The invention may be used with essentially any type of aerosol generator having a variable load, regardless of Q-factor. In some embodiments, the variable load is a resonant structure comprising an active piezoelectric element. Particular embodiments are configured as piezoelectric resonant structures.

A wide variety of atomizers include piezoelectric resonant structures and may therefore incorporate the techniques of the present invention. Merely by way of example, the invention may be used with atomizers, such as those described in U.S. Pat. Nos. 5,140,740, 5,938,117, 5,586,550 and 6,014,970, incorporated herein by reference. However, it will be appreciated that the invention is not intended to be limited only to these specific embodiments.

Particular embodiments of the present invention involve operating the aerosol generators at a desired frequency that produces the appropriate volumetric aerosolization rate and results in the most efficient operation. In some embodiments the desired frequency is the resonant frequency or a frequency near the resonant frequency, while in other embodiments this frequency is offset from the resonant frequency. Such an offset frequency can be either lower or higher than the resonant frequency. In one particular embodiment, the desired frequency is fa, which provides the highest volumetric rate for a given amount of input power.

Advantageously, aerosolization devices embodying the present invention aim to determine the instantaneous resonant frequency of the aperture plate during aerosolization of liquid in a highly reliable manner. In all cases, frequency is the variable that is swept and the voltage, current, impedance or phase difference, or any combination of these electrical variables or characteristics are tracked. An accurate determination of instantaneous resonant frequency may be accomplished by performing a high density of electrical variable sampling in the vicinity of the instantaneous resonant frequency. In other words, in the region of the instantaneous resonant frequency, electrical characteristics may need to be measured about every 100 Hz. However, when the frequency is far removed from the resonant frequency, electrical characteristics may need only be measured every 1–5 kHz. In other words, the density of electrical characteristic sampling may be much lower.

With the aerosolization devices of the invention, an indication of proximity to the instantaneous resonant frequency may be gained by comparing values of the electrical characteristics measured. Where there is little or no difference between measured values for two frequencies differing by a predetermined amount, any increment in frequency may be as large (or even larger) than the predetermined amount. However, when there is a difference between such measured values, the next increment in frequency is made smaller than the predetermined amount. The size of the next increment may be reduced proportionally to the change in characteristics. Further, if a reversal of phase between voltage and current is detected, the resonant frequency may have been passed. In such cases, the previous frequency may be returned to, and a smaller step selected. Other techniques that may be used to find the resonant frequency include step doubling, bisection, 1st and 2nd derivative tracking, and the like.

Referring now to FIG. 1, one embodiment of an aerosolization device 10 will be described. Device 10 comprises a housing 12 to hold the various components of aerosolization device 10. Housing 12 further includes a mouthpiece 14 and one or more vents (not shown) to permit air to enter into housing 12 when a user inhales from mouthpiece 14. Disposed within housing 12 is an aerosol generator 16 that comprises a cup-shaped member 18 to which is coupled an aperture plate 20. An annular piezoelectric element 22 is in contact with aperture plate 20 to cause aperture plate 20 to vibrate when electrical current is supplied to piezoelectric element 22. Aperture plate 20 is dome-shaped in geometry and includes a plurality of tapered apertures that narrow from the rear surface to the front surface. Exemplary aperture plates and aerosol generators that may be used in aerosolization device 10 are described in U.S. Pat. Nos. 5,086,785, 5,157,372 and 5,309,135 incorporated by reference.

Aerosolization device 10 further includes a canister 24 having a supply of liquid that is to be aerosolized by aerosol generator 16. Canister 24 may include a metering valve to place a metered amount of liquid onto aperture plate 20. Although not shown, a button or the like may be employed to dispense the volume of liquid when requested by the user.

Housing 12 includes an electronics region 26 for holding the various electrical components of aerosolization device 10. For example, region 26 may include a printed circuit board 28 which serves as a controller to control operation of the aerosol generator 16. More specifically, circuit board 28 may send (via circuitry not shown) an electrical signal to piezoelectric element 22 to cause aperture plate 20 to be vibrated. A power supply P, such as one or more batteries, is electrically coupled to circuit board 28 to provide aerosolization device 10 with power.

Figure 2:
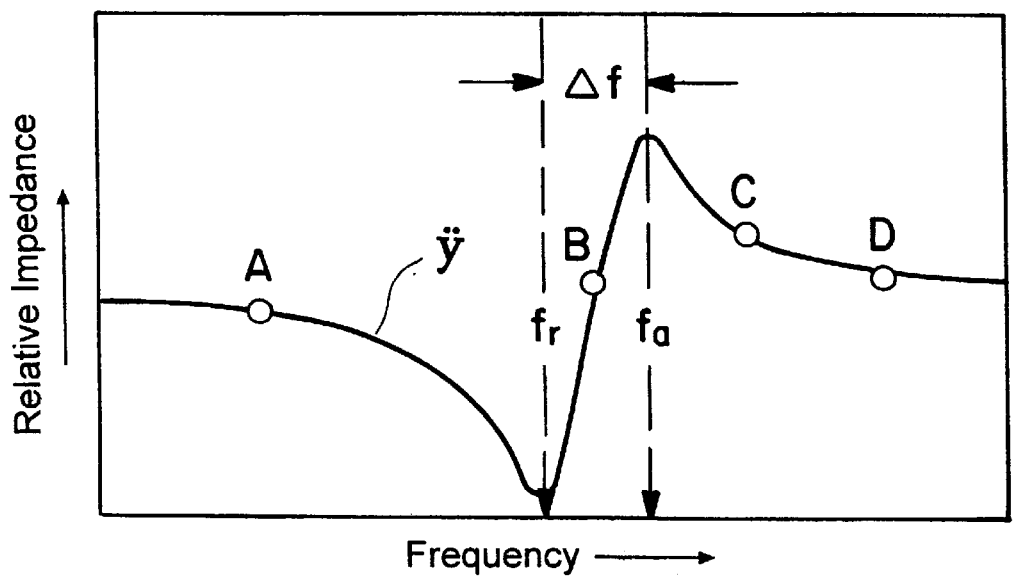
FIG. 2 is a graph showing typical impedance versus frequency plot of a piezoelectric-based electromechanical resonant structure.

FIG. 2 shows an impedance versus frequency plot for a typical resonant structure, such as a piezoelectric structure. In the plot, fr denotes the resonant frequency, and fa denotes anti-resonance with the difference in frequency between the two indicated by Δf. The basic character of the plot is largely independent of quality factor (Q=fr/Δf).

The basic character of the plot may be described as follows with reference to points A, B, C and D in FIG. 2, assuming a constant voltage driver source:

Frequency A refers to a point well below resonance where current has a lower magnitude less than that of the drawn signal at resonance. The current and voltage may have an unrelated phase difference.

Frequency fr refers to the resonance frequency of the stack. At resonance, current signal grows to its highest amplitude.

Frequency B refers to a drive frequency between resonance and anti-resonance. At this frequency, the current is less than the maximum current drawn at fr and ÿ, the phase angle, behaves similar to ÿ at fr.

Frequency fa refers to anti resonance frequency of the structure. At fa, a structure exhibits a high impedance and therefore does not draw much current.

Frequency C refers to a point beyond fa. At this frequency, the structure does draw a higher current than at anti-resonance. However, the ÿ between the current and the voltage is "flipped" or reversed in comparison to ÿ at frequency B. In other words, a circuit may recognize if it is operating at point B or C by comparing phase angles. At Point C ÿ would have a value closer to ÿ at resonance. And ÿ at point C could be over 180° off from ÿ at resonance.

Frequency D refers to a point beyond point C. Although impedance is lower at this point than at point C, its ÿ behaves similarly to ÿ at point C, and it may be recognized based on a similar technique to the one pointed out for frequency C recognition.

Figure 3:
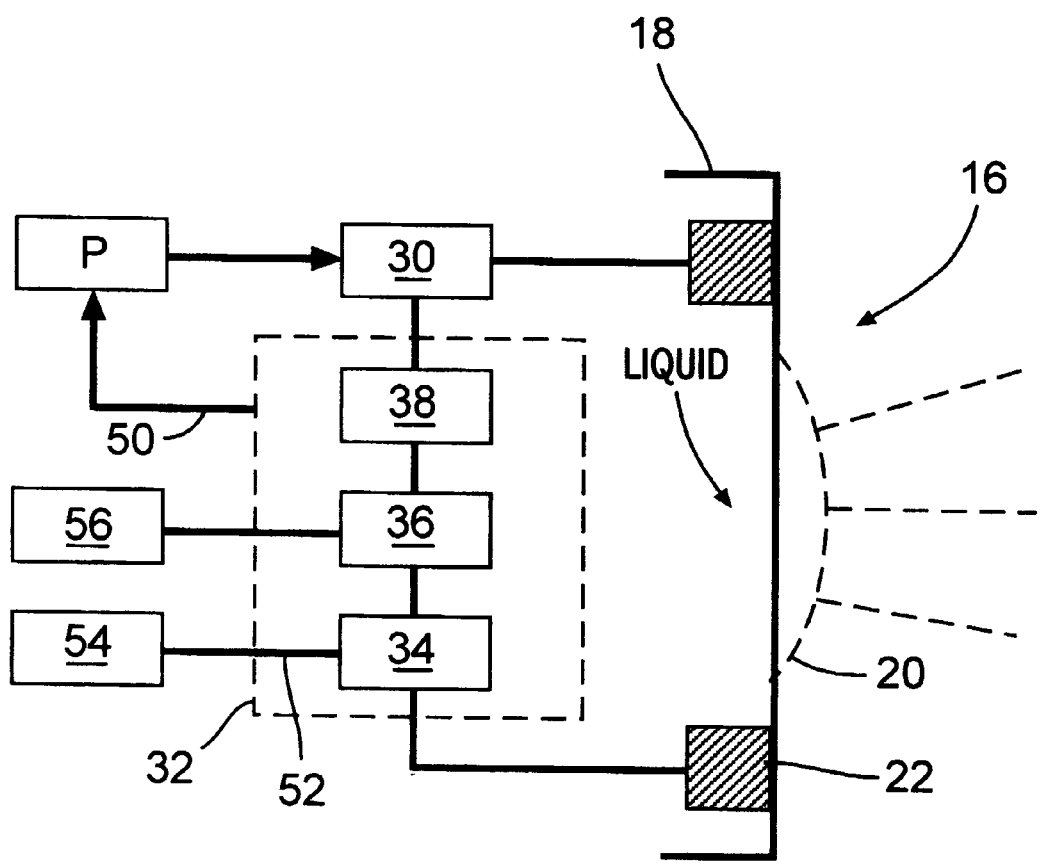
FIG. 3 is a schematic diagram of the aerosol generator of FIG. 1.

FIG. 3 is a schematic diagram showing detail of the aerosol generator 16. The piezoelectric element 22 is energized by an energizing unit 30 which is powered by power source P. The energizing unit 30 is capable of energizing the piezoelectric element 22 to vibrate the plate 20 across a range of frequencies. The energizing unit 30 is controlled by controller 32. The controller 32 is configured to control energization of the piezoelectric element 22 in order to vibrate the plate at its instantaneous resonant frequency or other desired frequency during aerosolization of supplied liquid through the aperture plate 20. The controller 32 includes a detector 34 for detecting values of an electrical characteristic, such as the electrical current I in the piezoelectric element when operating across a range of frequencies. Detected values for the electrical characteristic are compared by a comparator 36 and the results of the comparison are relayed to a selector 38. The selector 38 selects the magnitude of any change in vibrating frequency of the plate 20, and the controller 32 controls the energizing unit accordingly. The selector 38 makes its selection on the basis of the comparison made by comparator 36. For example, if the compared values are substantially equal, the selector 38 may increase vibrating frequency by a predetermined amount (i.e. a fixed frequency step or increment). On the other hand, if the compared values differ significantly, the selector 38 may increase vibrating frequency by a fraction of the predetermined amount. The fraction may be proportional to the relative difference between compared values. For instance, assuming a generally constant voltage, at each step the current and phase difference between current and voltage may be measured and compared. If compared current values differ significantly, the frequency step may be reduced in proportion to the change. If, however, the phase angle is "flipped", the resonant frequency may have been passed, and a smaller step may be selected. Hence, by also monitoring the difference in phase angles, the resonant frequency may be rapidly tracked.

Figure 4:
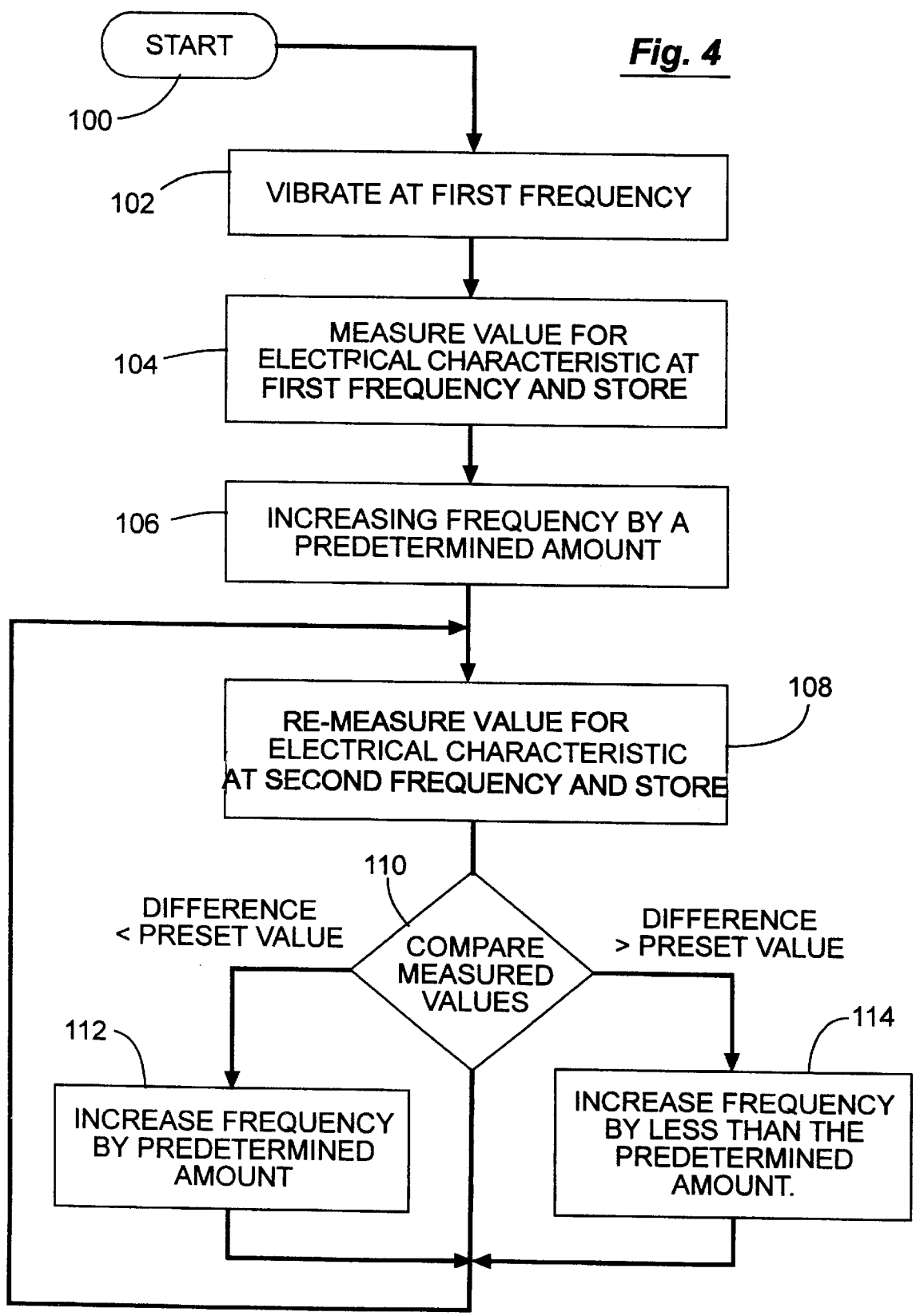
FIG. 4 is a flow chart illustrating a method for aerosolizing a liquid according to the invention.

FIG. 4 is a flow chart illustrating a method of operation of the aerosol generator in FIG. 1. When the device is actuated, it may optimally begin vibrating in "silent" mode where minimal power is consumed. When in the silent mode, an approximation of the resonant frequency under full power conditions may be determined. The frequency determined in the low power mode can be used to narrow the searching bandwidth covered to find the resonant or desired frequency when power is increased to aerosolize the liquid.

At the start 100, a frequency bandwidth (e.g. 10 kHz) around the vicinity of the as yet undetermined desired frequency for the device is selected. The desired frequency may then be determined by having controller 32 coordinate a rapid sweep through the frequency bandwidth to obtain the desired frequency. For example, at step 102, the aperture plate is vibrated at a first frequency well below the desired frequency. A value of one or more electrical characteristics (e.g., current and phase difference between voltage and current) of the piezoelectric element are measured and stored at 104. The vibrational frequency is changed at 106 by a predetermined amount. The value of the electrical characteristics for the new frequency are then re-measured and stored at 108. A comparison is then made at 110 between the two sets of values. If the difference between at least one of them (e.g. current) is below a preset value, the frequency is again increased 112 by an amount generally equal to the predetermined amount before repeating the measuring step 108. On the other hand, if the difference between the current values is greater than a preset value, the frequency is increased 114 but by an amount less than the predetermined amount before repeating the measuring step 108. Conveniently, the new frequency step may be inversely proportional to the magnitude of the change in current. In this way, as the current begins to rapidly change, the sampling size may decrease. The phase difference between voltage and current may also be compared to ensure that the resonant frequency has not been passed.

Hence, the desired frequency of the aperture plate may be determined readily and rapidly, particularly if the predetermined amount of frequency increment is relatively large (e.g. at least as great as the difference between anti-resonance and resonance frequencies). This is because as little time as possible is wasted repeating measurements in regions where there is little change in electrical characteristics. At the same time, there is little or no tendency to overlook the desired frequency altogether, since the frequency step size decreases (sampling rate increases/unit frequency) when approaching the resonant frequency to enable its accurate determination. This same procedure may then be used to find the desired frequency under increased power conditions when liquid is being aerosolized. However, a resonant frequency found when the aperture plate is operated in the silent mode may be used as a rough estimate of the desired frequency when operated at full power. Moreover, during operation the amount of liquid on the aperture plate may vary. Hence, the process may be repeated during aerosolization to maintain operation at the desired frequency.

Alternatively, the process illustrated in FIG. 4 may be used to determine a resonant frequency of the aperture plate when it is unloaded (not in contact with a liquid). The unloaded resonant frequency may be used as a rough estimate of the desired frequency when loaded. Again, the process may be repeated during aerosolization to maintain operation at the desired frequency as the amount of liquid on the plate is varied.

Further, determining the resonant frequency when the plate is unloaded can be used to determine if the device is degrading. For example, when the device is initially produced, the resonant frequency of the plate under unloaded conditions can be measured and recorded. Later, after the device has been in operation, the resonant frequency of the plate under unloaded conditions can be determined. This newly determined resonant frequency can be compared with the initially recorded resonant frequency. If the difference between the two frequencies is significant, a device failure may be indicated. Such a failure can include, but is not limited to, fluid clogging and/or a crack in the piezoelectric plate. This process of testing for device degradation can be repeated throughout the lifetime of the device to assure proper operation.

As previously mentioned, the controller 32 includes circuitry 50 to use minimal power prior to the supply of liquid to the aperture plate 20. The power consumption is increased when the supply of liquid to the aerosol generator commences. The resonant frequency for the unloaded aperture plate will generally be different to the instantaneous resonant frequency when the aperture plate is loaded with fluid for aerosolization. For instance, when a load such as drug fluid is placed on the aperture plate, its resonance and impedance characteristics change: frequency tends to decrease and impedance tends to increase. The instantaneous resonant frequency when the aperture plate is loaded is determined using the same iterative procedure with variable-sized frequency steps as described with reference to FIG. 4. However, the first frequency employed at step 102 may be based upon the resonant frequency of the unloaded aperture plate.

The difference in the resonant frequency for the unloaded aperture plate and the desired frequency for the aperture plate loaded with fluid may also be used to determine the end point of drug delivery. The controller 32 includes circuitry 52 for monitoring a change in a parameter, such as impedance, which is linked to device resonance. A sudden change in impedance occurs when the load on the aperture plate changes. A visible indicator 54 linked to the circuitry 52 will provide a visible sign to the user of the aerosol generator when the impedance drops below a threshold level. The visible sign will inform the user that drug delivery has been completed.

In some embodiments, differences in the resonant frequency are used to prevent "back puff". Specifically, back puff is the phenomena where a portion of the drug to be delivered is ejected back into the device rather than out of the device where it would be inhaled. Back puff occurs just prior to the end point of delivery when the aerosol generator is transitioning from a loaded to an unloaded state. To eliminate back puff, energy to the aerosol generator is reduced just prior to the transition from the loaded to an unloaded state.

In one embodiment where energy is reduced to avoid back puff, the resonant frequency is about 140 kHz when the aerosol generator is unloaded and about 135 kHz when loaded. As the aerosol generator aerosolizes the load, the resonant frequency begins to shift from the loaded frequency of 135 kHz to the unloaded frequency of 140 kHz. As this occurs and the frequency approaches 140 kHz, the voltage amplitude to the aerosol generator is reduced. Thus, when the end point of drug delivery is ascertained, the voltage applied to the aerosol generator has been reduced sufficiently to either eliminate or minimize back puff of the load still remaining on the aerosol generator. This advantageously minimizes the loss of drug during aerosol generation, improves overall efficiency, and reduces the cleaning requirements of the inhaler as less of the drug remains in the device.

The comparator 36 may also compare the selected value of the electrical characteristic with a range of reference values defining maximum and minimum acceptable operation. If the detected value should fall outside the range, warning device 56 will be activated to alert the user to potential gross device failure.

Figure 5:
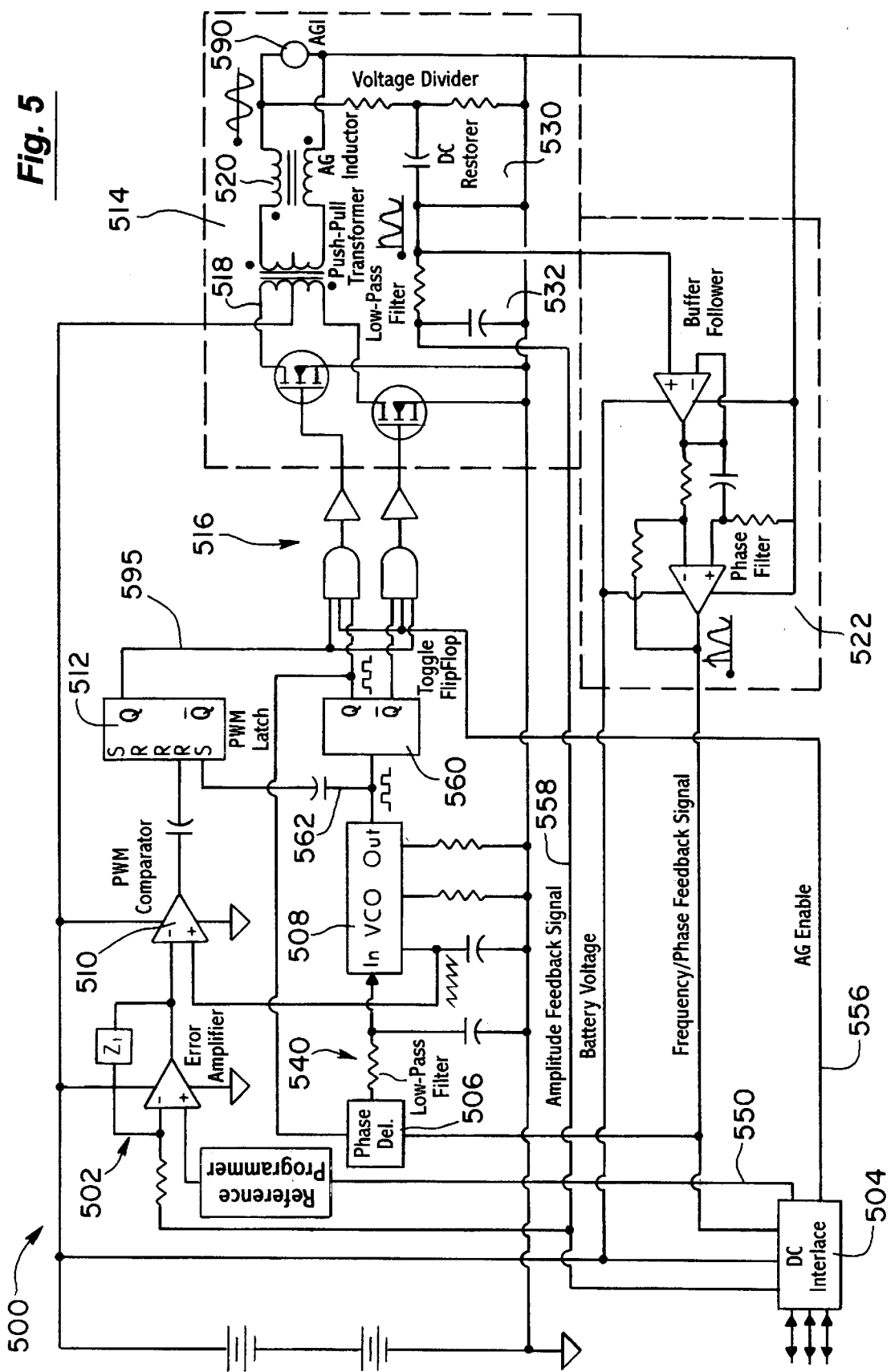
FIG. 5 is a circuit diagram of a phase locked loop (PLL) for tracking operation of a piezoelectric plate, and providing a frequency signal to the piezoelectric plate.

Controller circuit 32 can be implemented in either hardware, software, or a combination thereof. In some embodiments, controller circuit 32 comprises a phase locked loop (PLL) circuit as illustrated in FIG. 5. Referring to FIG. 5, a PLL circuit 500 comprises an error amplifier 502, a microprocessor interface 504, a phase detector 506, a frequency source 508, a comparator 510, a PWM latch 512, steering logic 516, a signal conditioner circuit 514, a toggle flip-flop 560, and a phase feedback circuit 522. Conditioner circuit comprises a push-pull transformer 518, a matching component 520, a voltage shift circuit 530, and a low pass filter 532.

In operation, error amplifier 502 amplifies a difference between an amplitude 558 of a signal driving an aerosol generator 590 and a desired amplitude 550 received from a microprocessor based controller (not shown) via microprocessor interface 504. The amplified difference is compared in comparator 510 to a reference frequency 554 from frequency source 508. Output from comparator 510 resets PWM latch 512 while an actual oscillator output 562 sets PWM latch 512. Actual oscillator output 562 is divided by two by toggle flip-flop 560. Both phases of the divided oscillator output 562 are input to steering logic 516. In addition, a set/reset output 595 from PWM latch 512 and an aerosol generator enable signal 556 are input to steering logic 516. The outputs from steering logic 516 drive signal conditioner 514. To provide an oscillating signal to signal conditioner 514, aerosol generator enable signal 556 must be asserted by the microprocessor based controller (not shown) via microprocessor interface 504.

Signal conditioner 514 receives a square wave output from steering logic 516 and creates a sinusoidal signal which drives the piezoelectric plate of aerosol generator 590. Amplitude feedback signal 558 is output from conditioner circuit 514 to error amplifier 502. In addition, conditioner circuit 514 drives phase shift circuit 522 which in turn creates a frequency and phase feedback signal 570. Phase detector 506 compares frequency and feedback signal 570 to the positive phase output of toggle flip-flop 560. The result of the comparison is fed to oscillator source 508 via a low pass filter 540 to either increase or decrease actual oscillator frequency 562 depending on the desired frequency.

Thus, by using a circuit similar to that described in relation to FIG. 5, generating the desired frequency for a piezoelectric plate is done iteratively with very little software control. Changes in desired frequency can then be monitored to detect changes in liquid loading or detect degradation in the device, as in the previously described embodiments.

The invention has now been described in detail for purposes of clarity of understanding. However, it will be appreciated that certain changes and modifications may be practiced within the scope of the appended claims.

What is claimed is:

1. A method for aerosolizing a liquid, comprising:
   providing an aerosol generator comprising a plate having a plurality of apertures therein and a piezoelectric element disposed to vibrate the plate;
   supplying a liquid to the plate;
   energizing the piezoelectric element to vibrate the plate at an initial frequency;
   adjusting energization of the piezoelectric element to vibrate the plate at a desired frequency during aerosolization of the liquid through the plurality of apertures;
   energizing the piezoelectric element at to vibrate the plate at its resonant frequency at a first power level prior to supplying the liquid to the plate; and
   increasing power level to a second power level when liquid is supplied to the plate.

2. A method according to claim 1, wherein the adjusting step comprises:
   detecting a first value of an electrical characteristic of the piezoelectric element at the initial frequency;
   energizing the piezoelectric element to vibrate the plate at a second frequency, the initial and second frequencies differing from each other by a predetermined amount;
   detecting a second value of the electrical characteristic of the piezo electric element at the second frequency; and
   comparing the first and second values of the electrical characteristics.

3. A method according to claim 2, wherein the electrical characteristic is selected from the group consisting of voltage, current and phase difference between voltage and current in the piezoelectric element.

4. A method according to claim 2, further comprising:
   energizing the piezoelectric element at a third frequency, the second and third frequencies differing from each other by an amount dependent upon the comparison between the first and second values of the electrical characteristic.

5. A method according to claim 4, wherein the amount is substantially equal to the predetermined amount when the first and second values of the electrical characteristic are substantially equal.

6. A method according to claim 4, wherein the amount is less than the predetermined amount when the first and second values of the electrical characteristic are substantially unequal.

7. A method according to claim 6, wherein the amount differs from the predetermined amount in inverse proportion to a difference between the first and second values of the electrical characteristic.

8. A method according to claim 4, further comprising:
  detecting a third value of the electrical characteristic of the piezoelectric element at the third frequency;
  comparing the second and third values of the electrical characteristic; and
  energizing the piezoelectric element at a fourth frequency, the third and fourth frequencies differing from each other by an amount dependent upon the comparison between the second and third values of the electrical characteristic.

9. A method according to claim 8, wherein the steps of detecting, comparing, and energizing are iterativley repeated.

10. A method according to claim 1, further comprising comparing a parameter indicative of instantaneous resonant frequency with a predetermined range of values.

11. A method according to claim 10, further comprising providing an indication when the parameter falls outside the predetermined range of values.

12. A method according to claim 1, wherein adjusting energization of the piezoelectric element is controlled by a phased locked loop circuit.

13. A method according to claim 1, wherein the desired frequency is the instantaneous resonant frequency of the plate.

14. A method according to claim 1, wherein the desired frequency is an anti-resonant frequency of the piezoelectric plate.

15. A method for aerosolizing a liquid, comprising:
  providing an aerosol generator comprising a plate having a plurality of apertures therein and a piezoelectric element disposed to vibrate the plate;
  supplying a liquid to the plate;
  energizing the piezoelectric element to vibrate the plate at an initial frequency;
  adjusting energization of the piezoelectric element to vibrate the plate at a desired frequency during aerosolization of the liquid through the plurality of apertures; and
  monitoring a parameter indicative of instantaneous resonant frequency to detect any rapid change in instantaneous resonant frequency.

16. A method according to claim 15, further comprising:
  reducing energy to the piezoelectric element upon detection of a rapid change in instantaneous resonant frequency, wherein back puff is reduced.

17. A method according to claim 15, further comprising:
  providing an indication upon detection of a rapid increase in instantaneous resonant frequency.

18. A method according to claim 17, wherein the indication is an end of dose indication.

19. A method according to claim 15, further comprising:
  reducing energization of the piezoelectric element upon detection of a rapid increase in instantaneous resonant frequency.

20. A method according to claim 15, wherein the parameter monitored is an impedance of the piezoelectric element.

21. A method according to claim 15, further comprising:
  energizing the piezoelectric element at to vibrate the plate at a resonant frequency at a first power level prior to supplying the liquid to the plate.

22. A method according to claim 21, further comprising:
  increasing power level to a second power level when liquid is supplied to the plate.

23. A method of controlling piezoelectric vibration in an apparatus comprising a piezoelectric vibrating element and a vibratable structure to which the piezoelectric vibrating element is attached, the method comprising:
  energizing the piezoelectric vibrating element to vibrate the vibratable structure at a first frequency;
  detecting a first value of an electrical characteristic of the piezoelectric vibrating element at the first frequency;
  energizing the piezoelectric vibratable element to vibrate the vibratable structure at a second frequency, the first and second frequencies differing from each other by a predetermined amount;
  detecting a second value of the electrical characteristic of the piezoelectric vibrating element at the second frequency;
  comparing the first and second values of the electrical characteristic; and
  energizing the piezoelectric element at a third frequency, the second and third frequencies differing from each other by a variable amount dependent upon the comparison made between the first and second values of the electrical characteristic.

24. A method according to claim 23, wherein the electrical characteristic is selected from the group consisting of voltage, current and phase difference between voltage and current in the piezoelectric vibrating element.

25. A method according to claim 24, wherein the variable amount is substantially equal to the predetermined amount when the first and second values of the electrical characteristic are substantially equal.

26. A method according to claim 25, wherein the variable amount is less than the predetermined amount when the first and second values of the electrical characteristic are substantially unequal.

27. A method according to claim 26, wherein the variable amount differs from the predetermined amount in inverse proportion to a difference between the first and second values of the electrical characteristic.

28. A method according to claim 23, further comprising:
  detecting a third value of the electrical characteristic of the piezoelectric vibrating element at the third frequency;
  comparing the second and third values of the electrical characteristic; and
  energizing the piezoelectric vibrating element at a fourth frequency, the third and fourth frequencies differing from each other by an amount dependent upon the comparison made between the second and third values of the electrical characteristic.

29. A method according to claim 23, wherein the apparatus comprises a piezoelectric structure.

30. A method according to claim 23, further comprising supplying a liquid to the vibratable structure.

31. A method of determining degradation of a piezoelectric vibration device, the method comprising:
  at a first time, determining a first resonant frequency of the a piezoelectric vibration device;
  at a second time, determining a second resonant frequency of the a piezoelectric vibration device; and
  comparing the first and second resonant frequencies to determine a difference, wherein the difference indicates degradation in the piezoelectric vibration device, wherein the degradation in the piezoelectric vibration device includes a crack in the piezoelectric vibration device;
  wherein the first and the second resonant frequencies are determined when the piezoelectric vibration device is not loaded with fluid.

32. A method of determining degradation of a piezoelectric vibration device, the method comprising:
   at a first time, determining a first resonant frequency of the a piezo electric vibration device;
   at a second time, determining a second resonant frequency of the a piezoelectric vibration device; and
   comparing the first and second resonant frequencies to determine a difference, wherein the difference indicates degradation in the piezoelectric vibration device, wherein the degradation in the piezoelectric vibration device includes a clog in the piezoelectric vibration device.

33. A method according to claim 32, wherein the first and the second resonant frequencies are determined when the piezoelectric vibration device is not loaded with fluid.

34. A method according to claim 32, wherein the degradation in the piezoelectric vibration device includes a crack in the piezoelectric vibration device.

35. A method for aerosolizing a liquid, comprising:
   providing an aerosol generator comprising a plate having a plurality of apertures therein and a piezoelectric element disposed to vibrate the plate;
   supplying a liquid to the plate;
   energizing the piezoelectric element to vibrate the plate at an initial frequency;
   adjusting energization of the piezoelectric element to vibrate the plate at a desired frequency during aerosolization of the liquid through the plurality of apertures;
   and comparing a parameter indicative of an instantaneous resonant frequency with a predetermined range of values.

36. A method for aerosolizing a liquid, comprising:
   providing an aerosol generator comprising a plate having a plurality of apertures therein and a piezoelectric element disposed to vibrate the plate;
   supplying a liquid to the plate;
   energizing the piezoelectric element to vibrate the plate at an initial frequency;
   adjusting energization of the piezo electric element to vibrate the plate at a desired frequency during aerosolization of the liquid through the plurality of apertures, the desired frequency being an instantaneous frequency of the plate.

37. A method of aerosolizing a fluid for inhalation, comprising:
   providing an aerosolizing device having an aerosolizing element, the aerosolizing element being vibrated to aerosolize a fluid, the aerosolizing device having a mouthpiece through which a user inhales aerosolized fluid;
   vibrating the aerosolizing element at a resonant frequency;
   measuring a first parameter related to the resonant frequency of the aerosolizing element during the vibrating step;
   delivering a volume of the fluid to the aerosolizing element;
   aerosolizing the fluid by vibrating the aerosolizing element, the aerosolized fluid being delivered to the user through the mouthpiece;
   measuring a second parameter related to the resonant frequency after initiating the aerosolizing step; and
   determining when the volume of fluid has been delivered by comparing the first and second parameters.

38. The method of claim 37, wherein:
   the measuring steps are carried out with the first and second parameters each being a parameter selected from the group of parameters consisting of frequency and impedance.

39. The method of claim 37, wherein:
   the measuring step for the first parameter is carried out before the delivering step.

40. The method of claim 37, further comprising the step of:
   vibrating the aerosolizing element after the delivering step at a power such that liquid is not aerosolized by the vibrating element.

41. The method of claim 37, wherein:
   the vibrating step is carried out with the aerosolizing element not being loaded with fluid.

* * * * *